United States Patent [19]

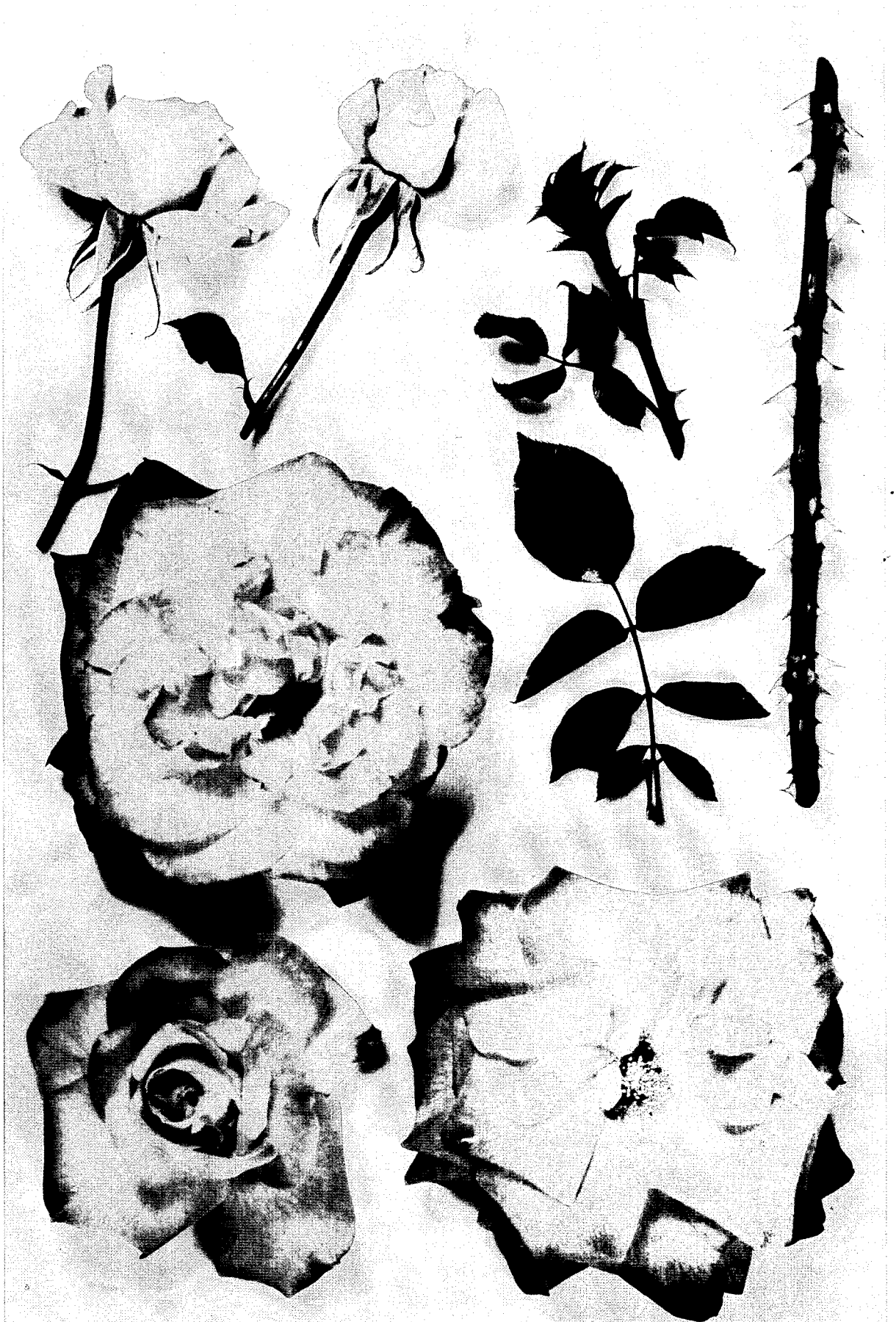

Delbard

[11] Plant 4,332

[45] Nov. 21, 1978

[54] ROSE PLANT—CAMARA

[75] Inventor: Georges A. Delbard, Paris, France

[73] Assignee: Jackson & Perkins Co., Medford, Oreg.

[21] Appl. No.: 859,450

[22] Filed: Dec. 12, 1977

[51] Int. Cl.[2] ..... A01H 5/00

[52] U.S. Cl. ..... Plt./20

[58] Field of Search ..... Plt./20

*Primary Examiner*—Robert E. Bagwill
*Assistant Examiner*—James R. Feyrer
*Attorney, Agent, or Firm*—Klarquist, Sparkman, Campbell, Leigh, Hall & Whinston

[57] ABSTRACT

A novel rose plant of the hybrid tea class, having vigorous and heavily branched stems, abundance and continuity of blooms with distinct color shadings.

8 Drawing Figures

1

The present invention relates to a new and distinct cultivar of rose plant of the hybrid tea class which was originated by me by crossing the cultivar [(Chic Parisien × Super Star) × (Gloire de Rome × Impeccable)] with pollen from the cultivar (Super Star × Samourai).

The primary objective of this breeding was to produce a cultivar of the hybrid tea class, particularly suitable for garden use, having an upright, vigorous plant, and producing flowers of a novel character, especially in color. This objective was substantially achieved along with other desirable improvements as evidenced by the following unique combination of characteristics which are outstanding in this new cultivar and which distinguish it from its parents as well as from all other cultivars of which I am aware:

1. A very vigorous, heavily branched, upright-growing plant of the hybrid tea class.

2. An abundance and continuity of flowers opening as Signal Red, changing slightly to Blood Red.

3. The veins of the flower petals generally are darker than interveinal areas, but as the flower opens, the distal portion of each petal darkens to near black in the interveinal areas, giving a distinctive shaded appearance to the petals.

Asexual reproduction of this new cultivar by budding as performed at Evry, France, and at Irvine, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart, except where ordinary dictionary significance of color is indicated.

Parentage:

*Seed parent.*—[(Chic Parisien × Super Star) × (Gloire de Rome × Impeccable)].

*Pollen parent.*—(Super Star × Samourai).

Classification:

*Botanical.*—Rosa Hybrid.

*Commercial.*—Hybrid Tea.

2

FLOWER

Observations made from specimens grown at Irvine, Calif., in August of 1977.

Blooming habit: Continuous.

Bud:

*Size.*—⅞" to 1" when petals start to unfurl.

*Form.*—Pointed ovoid.

*Color.*—When sepals first divide near Signal Red (719) overlaid with Oxblood Red (00823); when half blown, upper side of petals near Signal Red (719), lower side of petals, near Blood Red (820/3).

*Sepals.*—Color: Outer surface Scheele's Green (860) with a few irregularly shaped areas Garnet Brown (00918/3); inner surface Scheele's Green (860/3) with a little white tomentum. Three appendaged sepals lightly appendaged; two unappendaged sepals hairy edged.

*Receptacle.*—Color: Scheele's Green (860). Shape: Funnel. Size: Large. Surface: Smooth.

*Peduncle.*—Length: Short. Surface: Very slightly prickly. Color: Medium green, Garnet Brown (00918/3) on side exposed to direct sunlight. Strength: Stiff, heavy.

*Opening.*—Petals fold outward with very little recurving or quilling.

Bloom:

*Size.*—Large. Average open size 5".

*Borne.*—Singly or several together.

*Stems.*—Long.

*Form.*—When first open, high centered. Permanence, flattens.

*Petalage.*—Number of petals under normal conditions: 40.

*Color.*—Center of flower: Upper side of petals near Signal Red (719). Reverse side of petals: Near Blood Red (820/3). Base of petals: Small, well-defined area of Dresden Yellow (64/1). General tonality from a distance: Signal Red (719).

*Variegations.*—Veins are much darker, nearly black. Petal tips darken in irregular areas to nearly black.

*Discoloration.*—General tonality at end of first day, none; third day, darkened areas increase in size to approximately ⅓ of petal area.

*Fragrance.*—Very little.

Petals:

*Texture.*—Thick, leathery.
*Shape.*—Round.
*Form.*—Flat.
*Arrangement.*—Imbricated. Petaloids in center, many.
*Persistence.*—Drop off cleanly.
*Lastingness.*—On the plant, long. As cut flower, long.

Reproductive parts:
*Stamens, anthers.*—Large. Color, yellow. Arrangement, regular around styles.
*Filaments.*—Color: Crimson (22/1).
*Pollen.*—Gold yellow.
*Styles.*—Color: White, mottled with crimson streaks, sometimes all crimson.
*Stigmas.*—Color: White to Straw Yellow (604/2).

PLANT

Form: Bush.
Growth: Very vigorous, upright, branching.
Foliage: Number of leaflets on normal mid-stem leaves 5 or 7.
*Size.*—Medium.
*Quantity.*—Normal.
*Color.*—New foliage: Scheele's Green (860) heavily overlaid with Garnet Brown (00918/3). Old foliage: Near Spinach Green (0960).

Leaflets:
*Shape.*—Oval pointed.

*Texture.*—Leathery.
*Edge.*—Serrated.
*Serrations.*—Single.
*Petiole.*—Rachis: Color, mostly green. Underside: Prickles.
*Stipules.*—Long, bearded.
*Disease resistance.*—Normally resistant to mildew, blackspot, under normal growing conditions at Irvine, Calif.

Wood:
*New wood.*—Color: Bronzy Brown. Bark: Smooth
*Old wood.*—Color: Generally green with brown overtones. Bark: Smooth Prickles:
*Quantity.*—On main stalks from base, many. On laterals from stalk, many.
*Form.*—Oval base, long, hooked downward slightly.
*Color when young.*—Brown.
*Position.*—Irregular.

Small prickles:
*Quantity.*—On main stalks, none. On laterals, none.

I claim:

1. A new and distinct cultivar of rose plant of the hybrid tea class, substantially as herein shown and described, characterized particularly as to novelty by the unique combination of its vigorous upright plant, and its flower color of Signal Red to Blood Red with distinct darker veins and darker, almost black, shadings.

* * * * *

UNITED STATES PATENT OFFICE

CERTIFICATE OF CORRECTION

Patent No. PP 4,332 Dated November 21, 1978

Inventor(s) Georges Alphonse Delbard

It is certified that error appears in the above-identified patent and that said Letters Patent are hereby corrected as shown below:

The sheet of drawing should be deleted and the attached sheet of drawing substituted therefor.

Signed and Sealed this

*Twenty-second* Day of *May 1979*

[SEAL]

*Attest:*

RUTH C. MASON
*Attesting Officer*

DONALD W. BANNER
*Commissioner of Patents and Trademarks*